United States Patent [19]

Haxell et al.

[11] Patent Number: 5,573,946
[45] Date of Patent: Nov. 12, 1996

[54] **BIOLOGICALLY PURE CULTURE OF *STREPTOMYCES HYGROSCOPICUS* ATCC 53718 CAPABLE OF PRODUCING ANTIBIOTIC COMPOUNDS**

[75] Inventors: Mark A. Haxell, Broadstairs; David A. Perry, Sandwich, both of England; Hiroshi Maeda, Aichi; Junsuke Tone, Chita, both of Japan

[73] Assignee: Pfizer Inc., New York, N.Y.

[21] Appl. No.: 553,129

[22] Filed: Nov. 7, 1995

Related U.S. Application Data

[62] Division of Ser. No. 378,997, Jan. 27, 1995, Pat. No. 5,510,372, which is a continuation of Ser. No. 703,578, May 20, 1991, abandoned, which is a continuation of Ser. No. 314,734, Feb. 23, 1989, abandoned.

[30] Foreign Application Priority Data

Feb. 25, 1988 [GB] United Kingdom .................. 8804440

[51] Int. Cl.⁶ .............................. A01N 63/00; C12N 1/00; C12N 1/20; C12P 1/06
[52] U.S. Cl. ..................... 435/253.5; 424/93.43; 435/169; 435/261; 435/898
[58] Field of Search ......................... 424/93.43; 435/169, 435/253.5, 261, 898

[56] References Cited

U.S. PATENT DOCUMENTS

| | | | |
|---|---|---|---|
| 3,950,360 | 4/1976 | Aoki et al. ....................... | 260/343.2 R |
| 4,200,581 | 4/1980 | Fisher et al. .................... | 424/180 |
| 4,423,209 | 12/1983 | Mrozik ........................... | 536/7.1 |
| 4,806,527 | 2/1989 | Christensen et al. ............... | 514/30 |
| 5,045,457 | 9/1991 | Banks et al. ..................... | 435/124 |

FOREIGN PATENT DOCUMENTS

| | | | |
|---|---|---|---|
| 170006 | 2/1986 | European Pat. Off. . | |
| 184308 | 6/1986 | European Pat. Off. . | |
| 238258 | 9/1987 | European Pat. Off. . | |
| 254583 | 1/1988 | European Pat. Off. . | |
| 277916 | 8/1988 | European Pat. Off. . | |
| 0325462 | 7/1989 | European Pat. Off. ............... | 549/264 |
| 1390336 | 4/1976 | United Kingdom . | |
| 1573955 | 8/1980 | United Kingdom . | |
| 2166436 | 5/1986 | United Kingdom . | |
| 2176182 | 12/1986 | United Kingdom . | |

*Primary Examiner*—Michael G. Wityshyn
*Assistant Examiner*—Deborah K. Ware
*Attorney, Agent, or Firm*—Peter C. Richardson; Gregg C. Benson; Mervin E. Brokke

[57] ABSTRACT

The present invention relates to certain antibiotic compounds, designated N787-182 compounds herein and derivatives thereof, which are antiparasitic agents, active against insect pests, acari, free-living nematodes and endo- and ectoparasites. This invention also relates to pharmaceutical and other compositions containing such compounds, methods of using such compounds, the microorganism *Streptomyces hygroscopicus* ATCC 53718 and mutants or genetically transformed or recombinant form thereof, and processes for producing such compounds.

2 Claims, No Drawings

BIOLOGICALLY PURE CULTURE OF *STREPTOMYCES HYGROSCOPICUS* ATCC 53718 CAPABLE OF PRODUCING ANTIBIOTIC COMPOUNDS

This is a division of Ser. No. 08/378,997, filed on Jan. 27, 1995, now U.S. Pat. No. 5,860,582; which is a continuation of application Ser. No. 07/703,578, now abandoned, filed on May 20, 1991 as a continuation of application Ser. No. 07/314,734, filed on Feb 23, 1989, now abandoned.

BACKGROUND OF THE INVENTION

This invention relates to new antiparasitic agents and in particular to a series of novel macrolide antibiotics related to the milbemycins and avermectins, and to processes for their preparation and compositions thereof.

The avermectins and milbemycins form an important group of broad spectrum antiparasitic agents possessing anthelmintic, ectoparasiticidal, insecticidal, antibacterial, antifungal and growth promoting activity with application in the areas of animal and human health, agriculture and horticulture. The avermectins, previously known as the C-076 compounds are produced by fermentation of a strain of the microorganism *Streptomyces avermitilis* ATCC 31267, 31271 or 31272 under aerobic conditions in an aqueous nutrient medium containing inorganic sales and assimilable sources of carbon and nitrogen. The production, isolation and chemical structure of the eight individual components which make up the C-076 complex is described in British patent specification 1573955. The milbemycins are structurally related macrolide antibiotics lacking the sugar residues at the 13-position. They are produced by fermentation, for example using *Streptomyces hygroscopicus* spp *aureolacrimosus* B-41-146 as described in British patent specification 1390336 or using *Streptomyces cyaneogriseus* spp *noncyanogenus* NRRL 15773 as described in EP-A-0170006 or using *Streptomyces thermoarchaensis* NCIB 12015 as described in British patent application GB 2166436.

In the search for new antibiotics, structural modification of known antibiotics is attempted whenever possible. This approach is limited, however, to modifications which retain the desired activity. Many antibiotics, including the avermectins and milbemycins, have such complex structures that many changes can be difficult to make by chemical means. The discovery of new antibiotics produced by fermentation processes continues, therefore, to be of great importance even in cases where the antibiotic, once recognized, is quite similar to a previously known antibiotic.

We have now discovered a group of novel macrolide antibiotics collectively designated herein as N787-182, which are produced by culture of a novel microorganism of the genus Streptomyces as described herein, together with certain related compounds prepared from the N787-182 compounds by simple chemical transformation processes. The compounds possess a broad spectrum of activity against insect pests, acari, free-living nematodes and endo- and ectoparasites afflicting animals and humans.

SUMMARY OF THE INVENTION

Thus the present invention provides compounds having the following structure:

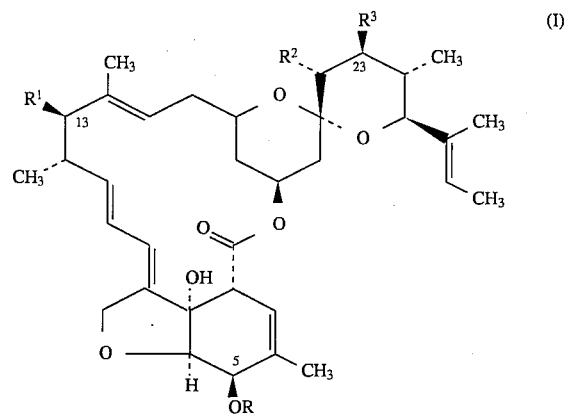

wherein the substituents R, $R^1$ $R^2$ $R^3$ and are as follows:

| Compound | R | $R^1$ | $R^2$ | $R^3$ |
| --- | --- | --- | --- | --- |
| N787-182-1 | $CH_3$ | OH | OH | H |
| N787-182-2 | H | OH | OH | $OCOCH(CH_3)_2$ |
| N787-182-3 | $CH_3$ | OH | OH | $OCOCH(CH_3)_2$ |
| N787-182-4 | H | $OCOCH(CH_3)_2$ | OH | H |
| N787-182-5 | $CH_3$ | $OCOCH(CH_3)_2$ | OH | H |
| N787-182-6 | H | $OCOCH(CH_3)_2$ | OH | $OCOCH(CH_3)_2$ |
| N787-182-7 | $CH_3$ | $OCOCH(CH_3)_2$ | OH | $OCOCH(CH_3)_2$ |
| N787-182-8 | H | H | OH | $OCOCH(CH_3)_2$ |
| N787-182-9 | H | $OCOCH(CH_3)_2$ | H | H |
| N787-182-10 | $CH_3$ | $OCOCH(CH_3)CH_2CH_3$ | OH | $OCOCH(CH_3)_2$ |
| N787-182-11 | $CH_3$ | H | OH | $OCOCH(CH_3)_2$ |
| N787-182-12 | $CH_3$ | $OCOCH(CH_3)_2$ | H | H |

The carbon skeleton of the above structure bears a close resemblance to that of the avermectins and milbemycins. However the various individual components defined above have never previously been obtained. In particular, certain of the N787–182 compounds are uniquely distinguished from the known natural milbemycins and avermectins in that they possess a beta-oxygen-linked substituent at C-13 (indicated by the solid wedge bond shown in formula I). This structural feature is important for the biological activities of these compounds. Other details of the stereochemistry have not been completely defined but the structure shown in formula (1) is proposed by analogy with known members of this class.

DETAILED DESCRIPTION OF THE INVENTION

The macrolide antibiotics N787-182 factors 1-12 are produced by the submerged aerobic fermentation in aqueous nutrient media of a microorganism isolated from a soil sample taken from Kinashiki City, Okayama Prefecture, Japan. The microorganism is assigned to the genus Streptomyces based on cell morphology and chemistry and is considered to be a new strain of *Streptomyces hygroscopicus* designated herein as Streptomyces sp ATCC 53718.

Certain of the N787-182 compounds may be obtained by interconversion using published chemical procedures. For example those compounds containing a methoxy substituent at the C-5 position may be converted to the corresponding C-5 hydroxy compounds. This reaction is performed by treating the 5-methoxy compound, or a suitably protected derivative thereof, with mercuric acetate and hydrolysing the resulting 3-acetoxy enol ether with dilute acid to give the 5-keto compound. This is then reduced using, for example, sodium borohydride to yield the 5-hydroxy derivative. Appropriate reagents and reaction conditions for these steps are described in U.S. Pat. No. 4,423,209. Thus, for example, N787-182 factor 12 may be converted into N787-182 factor 9 using this procedure. Conversely, compounds containing a 5-hydroxy group may be converted to the corresponding 5-methoxy derivative. This reaction is performed by treating the 5-hydroxy compound, or a suitably protected derivative thereof, with methyl iodide and silver (I) oxide in an inert solvent. Appropriate reagents and reaction conditions are described in the U.S. Pat. No. 4,200,581. By this means, for example, N787-182 factor 9 may be converted to N787-182 factor 12.

Those compounds lacking a substituent at the C-22 position may be obtained from the corresponding C-22 hydroxy compound, or a suitably protected derivative thereof, by an appropriate reductive procedure. For example, factor 5 may be reacted with p-tolylchlorothionoformate in the presence of a base such as pyridine, with or without addition of an inert solvent. The resulting C-22-thionocarbonate is then reacted with tri-n-butyltin hydride in an inert solvent in the presence of a suitable radical initiator such as azobisisobutyronitrile to give factor 12.

Those compounds lacking a substituent at C-13 may be oxidized at this position using the corresponding 5-keto compound as an intermediate. This may be prepared from the 5-methoxy compound by mercuric acetate treatment as described above or by oxidation of a 5-hydroxy compound, or a suitably protected derivative thereof, by manganese dioxide as described for example in EP-A-0238258. The 5-keto compound is then treated with selenium dioxide in a carboxylic acid as solvent such as formic acid to give a product containing a 13-beta-acyloxy substituent. If desired the 13-acyloxy group may be hydrolysed to a 13-hydroxy group by treatment with an acid or base, for example using hydrochloric acid or p-toluenesulphonic acid in a suitable organic solvent such as methanol or dioxane.

Alternatively the 13-acyloxy group may be hydrolysed by treatment with a Lewis acid, such as boron trifluoride in an alcohol solvent such as methanol to give the 13-hydroxy compound.

The 13-hydroxy group may in turn be acylated with a different carboxyl group by treatment with an acyl halide or anhydride in the presence of a base such as pyridine. Appropriate reagents and reaction conditions are described in EP-A-0184308. Finally the 5-keto group is reduced to a 5-hydroxy group using sodium borohydride as described above. Thus, using these procedures, for example N787-182 factor 8 may be converted to N787-182 factor 6, by way of N787-182 factor 2 as an intermediate.

Finally the acyl group at the 13-position may be removed from N787-182 factor 4, N787-182 factor 9 or N-787-182 factor 12 to give the corresponding novel 13-hydroxy compounds.

The ester cleavage may be achieved by several means including acid or base catalysed hydrolysis or by treatment with a reducing agent such as lithium aluminium hydride in an inert solvent such as diethyl ether or tetrahydrofuran at a temperature between −80° C. and 30° C., preferably −23° C.

Thus the present invention also provides compounds having the formula (I) above wherein the substituents are:

| Compound | R | $R^1$ | $R^2$ | $R^3$ |
|---|---|---|---|---|
| Compound 13 | H | OH | OH | H |
| Compound 14 | H | OH | H | H |
| Compound 15 | $CH_3$ | OH | H | H |

Preferred compounds on the basis of their antiparasitic activity are N787-182 factors 4, 6, 8 and 9.

The microorganism was characterised by planting from a slant onto ATCC no. 172 broth and incubating for our days at 28° C. on a shaker. It was then centrifuged for 20 minutes, washed three times with sterile distilled water and planted on media commonly used for identification of members of the Actinomycetales as hereinafter described. The culture was incubated at 28° C. and the results were read at varying times but most were commonly taken at 14 days. The colours are described in common terminology but exact colours were determined by comparisons with colour chips from the *Colour Harmony Manual*, fourth edition. The methods of whole-cell amino acid and sugar analyses are those described in Becker, Bet al, *Appl. Microbiol.*, 12, 421–423, 1964; and in Lechevalier, M. P., *J. Lab. Clin. Med.*, 71, 934–944, 1968.

Identification media used for the characterisation of the culture and references for their composition are as follows:
1. Tryptone-Yeast Extract Broth—(ISP medium no. 1, Difco).
2. Yeast Extract-Malt Extract Agar—(ISP medium no. 2, Difco).
3. Oatmeal Agar—(ISP medium no. 3, Difco).
4. Inorganic Salts-Starch Agar—(ISP medium no. 4, Difco).
5. Glycerol-Asparagine Agar—(ISP medium no. 5, Difco).
6. Peptone-Yeast Extract Iron Agar—(ISP medium no. 6, Difco).
7. Czapek-Sucrose Agar—S. A. Waksman, The Actinomycetes, Vol. 2, medium no 1, p 328, 1961.
8. Glucose-Asparagine Agar—Ibid, medium no. 2, p. 328.
9. Bennett's Agar—Ibid, medium no. 30, p. 331.
10. Emerson's Agar—Ibid, medium no. 28, p. 331.
11. Nutrient Agar—Ibid, medium no.14, p. 330.
12. Gordon and Smith's Tyrosine Agar—R. E. Gordon and M. M. Smith, J. Bact, 69,147–150, 1955.
13. Casein Agar—Ibid.
14. Gelatin Agar—R. E. Gordon and J. M. Mihm, J. Bact., 73,15–27, 1957.
15. Starch Agar—Ibid.
16. Organic Nitrate Broth—Ibid.
17. Potato Carrot Agar—M. P. Lechevalier, J. Lab. and Clin. Med., 71,934–944, 1968, but use only 30 g potatoes, 2.5 g carrots and 20 g agar.
18. 2% Tap Water Agar.

19. Dextrose Nitrate Broth—S. A. Waksman, The Actinomycetes, Vol. 2, medium no. 1, p. 328, 1961, with 3 g dextrose substituted for 30 g sucrose and agar omitted.
20. Cellulose Utilization
   a) H. L. Jensen, *Proc. Linn, Soc. N.S.W.*, 55, 231–248, 1930.
   b) M. Levine and H. W. Schoenlein, A Compilation of Culture Media, medium no. 2511, 1930.
21. Skimmed Milk—Difco.
22. Carbohydrate utilisation—(ISP medium no. 9, Difco).
23. Temperature Range—ATCC medium 172 in ATCC Culture Collection Catalogue, 15th ed., p. 608, 1982.

The observations of growth and appearance of the organism were as follows:

Yeast Extract-Malt Extract Agar

Growth good, pale yellowish brown, yellowish, yellowish grey to grey (3 ec, 1½ ea, 1½ ec, 1½ ge, 1½ ig); raised, wrinkled; aerial mycelium yellowish, yellowish grey to grey (1½ ea, 1½ ec, 1½ ge, 1½ ig); reverse pale yellowish brown (3 gc); soluble pigment yellowish brown (3 lc).

Oatmeal Agar

Growth moderate; cream, pale grey, grey, pink-grey, dark grey to black ( 2 ca, near grey series 3 dc, 3 fe, 5 fe, 3 ml, 3 po); slightly raised, smooth to granular; aerial mycelium pale grey, grey, pink-grey, dark grey to black (near grey series 3 dc, 3 fe, 5 fe, 3 ml, 3 po) with some hygroscopic patches; reverse cream, grey, dark grey to black (2 ca, near grey series 3 fe, 3 ml, 3 po); soluble pigment cream to pale yellowish (2 ca, 2 ea).

Inorganic Salts-Starch Agar

Growth moderate, cream (2 ca); with pale yellowish, pale grey to dark grey (2 ca, 2 ea, near gray series 3 dc, 3 fe, 3 ih, 3 ml) aerial mycelium; slightly raised, smooth to granular, may be slightly wrinkled toward edge; reverse cream, pale grey, grey to dark grey (2 ca, near grey series 3 fe, 3 ih, 3 ml, 3 dc); soluble pigment pale yellowish (2 ia).

Glycerol-Asparagine Agar

Growth poor, cream (2 ca), thin, smooth, no aerial mycelium; reverse cream (2 ca); no soluble pigment.

Czapek-Sucrose Agar

Growth moderate, cream (2 ca), thin, smooth, with a few patches of white aerial mycelium; reverse cream (2 ca); soluble pigment cream (2 ca).

Glucose-Asparagine Agar

Growth good, cream (2 ca); with white, pale yellow, yellow, pale grey, grey, pink-grey to dark grey (1½ ea, 1½ ga, near grey series 3 dc, 3 fe, 5 fe, 3 ih) aerial mycelium; slightly raised, wrinkled; reverse cream, pale yellow, pale grey to grey (2 ca, 2 ea, near grey series 3 dc, 3 fe, 3 ih); soluble pigment pale yellowish (2 ea).

Gordon and Smith's Tyrosine Agar

Growth moderate, brown (4 lg), slightly raised, smooth to slightly wrinkled, with a few small dots of white aerial mycelium; reverse pale yellowish brown (3 gc); soluble pigment dark brown (4 ni).

Casein Agar

Growth moderate, tan to pale pink-brown (3 ec, 4 ec), slightly raised, smooth to slightly wrinkled, no aerial mycelium; reverse pale yellowish brown (3 gc); soluble pigment yellowish brown (3 lc).

Bennett's Agar

Growth good; cream, pale yellowish, pale grey, grey, pink-grey to dark pink-grey (2 ca, 2 ea, near grey series 3 dc, 3 fe, 5 fe, 3 ih, 5 ih, 5 ml); raised, wrinkled, aerial mycelium same as surface; reverse pale yellowish, pale grey to dark grey (2 ea, near grey series 3 dc, 3 e, 3 ih, 3 ml); soluble pigment pale yellowish (2 ga).

Emerson's Agar

Growth good, tan (3 ec), raised, wrinkled, with a few dots of white aerial mycelium; reverse pale yellowish brown (3 gc); soluble pigment yellowish brown (3 lc).

Nutrient Agar

Growth poor to moderate, cream (2 ca), slightly raised, smooth to slightly wrinkled, no aerial mycelium; reverse cream (2 ca); no soluble pigment.

Gelatin Agar

Growth moderate to good, cream (2 ca), slightly raised, smooth but wrinkled toward edge, no aerial mycelium; reverse cream (2 ca); no soluble pigment.

Starch Agar

Growth moderate to good, cream to tan (2 ca, 3 ec), with some, dots of white aerial mycelium, slightly raised. wrinkled; reverse pale yellowish, yellowish brown to brown (2 ea, 3 gc, 3 ie); no soluble pigment.

Potato Carrot Agar

Growth moderate; cream, pale grey to pink-grey (2 ca, near grey series 3 dc, 3 fe, 3 ih); slightly raised, reverse cream to grey (2 ca, near grey series 3 fe, 3 dc); no soluble pigment.

Tap Water Agar

Growth poor, pale grey To grey (near grey series 3 dc, 3 fe), thin, smooth, aerial mycelium same as surface; reverse cream, pale grey to grey (2 ca, near grey series 3 dc, 3 fe); no soluble pigment.

Morphological Properties

The morphological properties were observed after two weeks of incubation on potato carrot agar: spore mass in grey colour-series; spore chains in section spirales, tightly coiled or slightly open, of small diameter, up to seven turns per spore chain, may aggregate into hygroscopic masses; sporophores monopodially branched; spores short rod-shaped, rod-shaped, or angular, 1.2–1.8×0.9–1.2 µm; warty, as revealed by scanning electron microscopy.

Biochemical Properties

Melanin not produced in tryptone-yeast extract broth; hydrogen sulphide produced on peptone-yeast extract iron agar; gelatin liquefied; starch hydrolyzed; nitrate not reduced to nitrite in either organic nitrate broth or dextrose nitrate broth; good growth but no disintegration on both cellulose broths; coagulation and peptonization on milk. Carbohydrate utilization: glucose, arabinose, fructose, inositol, mannitol, raffinose, rhamnose, sucrose and xylose utilized.

Temperature Relations

| 21° C. | 28° C. | 37° C. | 45° C. |
| --- | --- | --- | --- |
| Good Growth | Good Growth | Good Growth | No Growth |

Cell Wall Analysis

The whole-cell hydrolysates contained LL-diaminopimelic acid and mannose.

The culture is characterised by the grey spores in mass, the negative melanin reaction, and the warty spores which are arranged in spirally coiled chains. The spore chains may coalesce into hygroscopic masses. The culture utilized glucose, arabinose, fructose, inositol, mannitol, raffinose, rhamnose, sucrose, and xylose. The whole-cell hydrolysate indicates the presence of LL-diaminopimelic acid and the absence of diagnostic sugars.

On the basis of the data mentioned above and in accordance with a broader species concept published by Tresner and Backus in *Appl. Microbiol.*, 4:243–250, 1956, the culture is considered to be a new strain of *Streptomyces*

*hygroscopius* (Jensen) Waksman & Henrici. It has been deposited at the American Type Culture Collection, 12301 Parklawn Drive, Rockville, Md. 20852, U.S.A. under the provisions of the Budapest Treaty on 27th January, 1988 under the accession number ATCC 53718.

Cultivation and isolation of antibiotics N787-182 may be conducted under conditions similar to those generally employed to produce antibiotics by fermentation. Cultivation may take place in an aqueous nutrient medium containing suitable sources of carbon, nitrogen and trace elements for a period of several days under aerobic conditions at a temperature in the range of 24° to 36° C. As with the majority of antibiotic fermentations the amounts and proportions of N787-182 compounds will vary with changing fermentation conditions especially with regard to nutrient components, aeration conditions and pH. The mycelial product is then recovered by centrifugation or filtration and extracted with acetone or methanol. The solvent extract is concentrated and the desired products are extracted into a water-immiscible organic solvent, such as methylene chloride, ethyl acetate, chloroform, butanol or methyisobutyl ketone. The solvent extract is concentrated and the crude products of formula (I) are further purified as necessary by chromatography. Final purification and separation of the individual components can be achieved by repeated column chromatography or using a technique such as reverse phase high pressure liquid chromatography (HPLC).

Alternatively, cultivation may take place on agar plates of a suitable medium under aerobic conditions at a temperature in the range of 24° to 36° C. for several days. The agar is then extracted with an organic solvent such as methanol, filtered and the filtrate concentrated. Further enrichment and separation of the N787-182 antibiotics of formula (I) is then carried out as described above.

The macrolide antibiotics N787-182 are generally obtained as a mixture of compounds having the formula (I) wherein R, $R^1$ $R^2$ and $R^3$ are as previously defined; however the proportions of the factors 1–12 can vary depending on the particular fermentation conditions employed.

Thus the present invention provides a process for producing the N787-182 antibiotic compounds of the formula (I) as herein defined, which comprises cultivating the microorganism Streptomyces sp ATCC 53718, or a mutant, genetically transformed or recombinant thereof having the ability to produce one or more of the N787-182 antibiotics, in submerged aqueous or solid agar culture media containing an assimilable source of carbon, nitrogen and inorganic salts, under submerged aerobic fermentation conditions until a recoverable amount of said antibiotic is obtained.

The term mutant includes any mutant strain which arises spontaneously or by the application of known techniques, such as exposure to ionising radiation, ultraviolet light, and/or chemical mutagens such as N-methyl-N-nitroso-urethane, nitrosoguanidine and ethane methane sulphate, etc. Genetically transformed-and recombinant forms include mutants and genetic variants produced by genetic engineering techniques, including for example recombination, transformation, transduction, and protoplast fusion, etc.

As previously mentioned the compounds of the invention are highly active antiparasitic agents having particular utility as anthelmintics, ectoparasiticides, insecticides, acaricides and animal growth promotants.

Thus the compounds are effective in treating a variety of conditions caused by endoparasites including, in particular, helminthiasis which is most frequently caused by a group of parasitic worms described as nematodes and which can cause severe economic losses in swine, sheep, horses and cattle as well as affecting domestic animals and poultry. The compounds are also effective against other nematodes which affect various species of animals including, for example, Dirofilaria in dogs and various parasites which can infect humans including gastro-intestinal parasites such as Ancylostoma, Necator, Ascaris, Strongyloides, Trichinella, Capillaria, Trichuris, Enterobius and parasites which are found in the blood or other tissues and organs such as filiarial worms and the extra intestinal stages of Strongloides and Trichinella.

The compounds are also of value in treating ectoparasite infections including in particular arthropod ectoparasites of animals and birds such as ticks, mites, lice, fleas, blowfly, biting insects and migrating dipterous larvae which can affect cattle and horses.

The compounds are also insecticides active against household pests such as the cockroach, clothes moth, carpet beetle and the housefly as well as being useful against insect pests of stored grain and of agricultural plants such as spider mites, aphids, caterpillars and against migratory orthopterans such as locusts.

The compounds of formula (I) are administered as a formulation appropriate to the specific use envisaged and to the particular species of host animal being treated and the parasite or insect involved. For use as an anthelmintic the compounds are preferably administered by injection, either subcutaneously or intramuscularly, alternatively they may be be administered orally in the form of a capsule, bolus, tablet or liquid drench, or they may be administered as a pour-on formulation or as an implant. Such formulations are prepared in a conventional manner in accordance with standard veterinary practice. Thus capsules, boluses or tablets may be prepared by mixing the active ingredient with a suitable finely divided diluent or carrier, additionally containing a disintigrating agent and/or binder such as starch, lactose, talc, or magnesium stearate. A drench formulation may be prepared by dispersing the active ingredient in an aqueous solution together with dispersing or wetting agents and injectable formulations may be prepared in the form of a sterile solution or emulsion. These formulations will vary with regard to the weight of active compound depending on the species of host animal to be treated, the severity and type of infection and the body weight of the host. Generally for oral administration a dose of from about 0.001 to 10 mg per Kg of animal body weight given as a single dose or in divided doses for a period of from 1 to 5 days will be satisfactory but of course there can be instances where higher or lower dosage ranges are indicated and such are within the scope of this invention.

As an alternative the compounds may be administered with the animal feedstuff and for this purpose a concentrated feed additive or premix may be prepared for mixing with the normal animal feed.

For use as an insecticide and for treating agricultural pests the compounds are applied as sprays, dusts, pour-on formulations, emulsions and the like in accordance with standard agricultural practice.

For use as a growth promotant or for improving the lean meat to fat ratio in farm or domestic animals, the compounds may be administered with the animal feedstuff or drinking water. Alternatively they may be administered orally in the form of a capsule, bolus, tablet or liquid drench, or parenterally by injection or as an implant. Such formulations are prepared in a conventional manner in accordance with standard veterinary practice.

For human use the compounds are administered as a pharmaceutically acceptable formulation in accordance with normal medical practice.

The invention is illustrated by the following Examples in which Examples 1–9 describe the preparation, isolation and identification of the N787-182 actors 1–12 of formula (I), Examples 10–14 illustrate chemical transformations including the preparation of compounds 13–15, and Examples 14 and 15 illustrate their anthelmintic and insecticidal activity.

In the following Examples:

Oxoid peptone and Oxoid Lab Lemco were supplied by Oxoid Limited, Wade Road, Basingstoke, Hampshire, U.K.

Ultraviolet spectra were recorded on line using a Hewlett-Packard HP 1090 diode-array detector (Table 2).

Electron impact mass spectroscopy was performed using a VG model 7070F mass spectrometer (Table 3).

Fast atom bombardment mass spectroscopy was performed using a VG model 7070E mass spectrometer (Table 4). Samples were introduced using a matrix consisting of glycerol, thioglycerol, sodium chloride and water.

ACE mass spectroscopy was performed using a VG model 7070E mass spectrometer ($CH_4$ reagent gas) (Table 5).

Nuclear magnetic resonance spectral data were obtained using a Nicolet QE300 or a General Electric GN50Q spectrometer (Table 6).

EXAMPLE 1

Agar Fermentation of *Streptomyces Hygroscopicus* Sp ATCC 53718

A mycelial preparation of *Streptomyces hygroscopicus* sp ATCC 53718 (2 ml) which had been stored at −80° C. in 10% (v/v) aqueous glycerol was inoculated into 100 ml of a sterile medium containing beef extract (0.3 g), polypeptone (0.5 g), glucose (0.1 g), dextrin (2.4 g), yeast extract (0.5 g), calcium carbonate (0.4 g) in tap water at pH 7. This was incubated in a 300 ml Erlenmeyer flask at 28° C. on a rotary shaker operating at 200 rpm for 3 days. Five ml of this inoculum was added to 100 ml of a melted agar medium kept at 45°–50° C., prepared by dissolving corn starch (18 g), soybean meal (12.5 g), $MgSO_4.7H_2O$ (0.25 g), $KH_2PO_4$ (0.5 g), $Na_2HPO_4.12H_2O$ (,3.1 g), $CoCl_2.6H_2O$ (2.5 mg), $FeSO_4.7H_2O$ (5 mg), cottonseed oil (8.35 g) and agar (18 g) in deionised water (1 liter) at pH 7. This was then poured onto 400 ml of the same agar medium which had been allowed to solidify on a plate (255×255 mm). This plate was then incubated at 28° C. for 10 days.

A total volume of 3 liters of agar fermented in this manner was extracted with methanol, filtered and concentrated to an aqueous suspension. This was extracted with ethyl acetate and the organic layer was concentrated to an oily residue. This crude material was dissolved in methanol (50 ml) and stored overnight at −2° C. before filtering and evaporating to give a dark oil (2.05 g). This material (1.85 g) was chromatographed on silica gel (80 g Kieselgel 60, 230–400 mesh, Merck) eluting initially with a 4:1 mixture of dichloromethane and ethyl acetate followed by a 1:1 mixture of these solvents and finally with ethyl acetate. A total of ten fractions were collected, evaporated under vacuum and analysed using an Ultrasphere-ODS (Trademark Beckman) 5 m HPLC column (4.6×250 mm) eluting with a methanol-water gradient with UV detection at 243 nm. The individual N787-182 factors were then isolated from the appropriate product containing fractions by further HPLC as described in the Examples 4 to 7.

EXAMPLE 2

Shake Flask Fermentation of *Streptomyces Hygroscopicus* sp ATCC 53718

A vial containing *Streptomyces hygroscopicus* sp ATCC 53718 mycelia stored at −70° C. in 20% (v/v) aqueous glycerol (1.8 ml) was allowed to thaw and used to inoculate 50 mls of a sterile medium consisting of glucose (0.05 g), starch (1.2 g), Oxoid peptone (0.25 g) yeast extract (0.25 g), Lab Lemco (0.15 g) and calcium carbonate (0.2 g) contained in a 300 ml Erlenmeyer flask. This was incubated at 28° C. on a rotary shaker operating at 170 rpm for 1 day, after which time 1 ml aliquots were used to inoculate 50 mls of a medium consisting of starch 0.5 g), 3-(N-morpholino)propanesulfonic acid (1.0 g), soyabean meal (0.625 g), cottonseed oil (0.42 g) $Na_2HPO_4.12\ H_2O$ (0.15 g) $KH_2PO$ (0.025 g) $MgSO_4.7HO$ (0.01 g), $FeSO.7H_2O$ (10 µg) and $CoCl_2.6H_2O$ (5 µg) which is adjusted to pH 6.7 by addition of sodium hydroxide, contained in 300 ml flasks. These flasks were incubated for 10 days on a shaker as above at 28° C.

The fermentation broths were combined and the mycelium recovered by filtration. The mycelial cake was agitated with acetone and methylene chloride was added. The mixture was filtered and the solution evaporated to give a dark oil. Analysis of this material by HPLC as described in Example 1 showed that it contained a mixture of the N787-182 factors similar to that obtained in Example 1.

EXAMPLE 3

Submerged Fermentation of *Streptomyces Hygroscopicus* sp. ATCC 53718

Two vials containing *Streptomyces hygroscopicus* ATCC 53718 mycelia stored at −70° C. in 20% (v/v) aqueous glycerol (1.8 ml) were allowed to thaw and used to inoculate two 300 ml Erlenmeyer flasks each containing 50 ml of a sterile medium consisting of glucose (0.05 g), starch (1.2 g), Oxoid peptone (0.25 g), yeast extract (0.25 g), Lab Lemco (0.15 g) and calcium carbonate (0.2 g). These were incubated at 28° C. on a rotary shaker operating at 170 rpm for one day after which time 40 mls was removed from each flask and used to inoculate two 3 liter flasks each containing 700 ml of a medium consisting of glucose (0.7 g), starch (16.8 g), Oxoid peptone (3.5 g), yeast extract (3.5 g), Lab Lemco (2.25 g) and calcium carbonate (2.8 g). These flasks were incubated as above for one day and used to inoculate a 100 liter fermenter containing 70 liters of a medium consisting of starch (700 g), soyabean meal (875 g), cottonseed oil (584.5 g), $MgSO_4.7H_2O$ (35 g), $KH_2PO_4$ (35 g) $Na_2HPO_4.12H_2O$ (217 g), $CoCl_2.6H_2O$ (0.35 g), $FeSO_4.7H_2O$ (0.35 g) and 3-(N-morpholino)-propane sulphonic acid (1.4 kg) adjusted to pH 6.7 by addition of sodium hydroxide. This fermenter was operated at 28° C. with an agitation speed of 200 rpm and an air flow of 35 liters per minute for 12 days. Excessive foaming was controlled by addition of polypropylene glycol (molecular weight 2000).

The mycelium was recovered by filtration and extracted with acetone (2×50 liters). The solution was evaporated to give an aqueous suspension which was extracted with ethyl acetate (3×10 liters). This extract was evaporated to give an oily residue which was analysed and purified by an equivalent procedure to that described in Example 1. The fractions collected from the silica column chromatography were analysed by HPLC and evaporated under vacuum. Fractions containing the desired N787-182 factors were then further processed as described in the Examples 8 and 9.

EXAMPLE 4

Isolation of N787-182 - 1, 2 and 3

Fraction 9 as obtained by the method described in Example 1 was found to contain N787-182 factors 1, 2 and 3 by HPLC. This material (44.7 mg) was chromatographed on an Ultrasphere-ODS (5 μm) (Trademark-Beckman) HPLC column (10×250 mm) eluting with water:methanol 25:75 at 3 mls per minute. Fractions eluting between 12 and 15 minutes contained N787-182 - 1, between 18 and 20 minutes N787-182 - 2 and between 24 and 28 minutes N787-182 - 3. The appropriate fractions were combined, evaporated under vacuum and the components were characterised by their chromatographic and spectroscopic properties as summarised in Tables 1–6 following.

EXAMPLE 5

Isolation of N787-182-5, 7, 10 and 11

Fraction 4 as obtained by the method described in Example 1 was found to contain N787-182 factors 5, 7, 10 and 11 by HPLC. This material (136 mg) was chromatographed on a C18 Zorbax ODS (8 m) (Trademark, Dupont) HPLC column (21.2×250 mm) eluting with methanol:water 82:18 at 9 mls per minute Fractions eluting between 30 and 32 minutes contained N787-182-5, between 40 and 44 minutes N787-182-7, between 52 and 55 minutes N787-182-10 and between 55 and 65 minutes N787-182-11. The appropriate fractions were combined, evaporated under vacuum and the components, were characterised by their chromatographic and spectroscopic properties as summarised in Tables 1–6.

In addition compound N787-182-5 gave a characteristic carbon-13 nuclear magnetic resonance spectrum in deuterochloroform with peaks at the following chemical shifts in parts per million relative to tetramethylsilane: 176.44, 173.93, 141.34, 137.55, 136.19, 135.89, 134.06, 125.88, 124.84, 124.07, 119.42, 118.56, 99.04, 83.45, 82.23, 80.57, 77.75, 77.01, 71.72, 68.70, 68,38, 67.62, 58.00, 45.71, 40.11, 37.05; 36.58, 36.50, 34.61, 34.49, 32.21, 20.10, 19.16 (two unresolved signals), 18.79, 17.64, 13.29, 11.14 and 11.07.

EXAMPLE 6

Isolation of N787-182-4 and 8

Fractions 7 and 8 as obtained by the method described in Example 1 both contained N787-182 factors 4 and 8 by analytical HPLC and were combined. This material (160 mg) was chromatographed on a C18 Zorbax ODS (8 m) (Trademark, Dupont) HPLC column (21.2×250 mm) eluting with methanol:water 82:18 at 9 mls per minute. Fractions eluting between 25 and 30 minutes contained N787-182-4 and between 37 and 45 minutes N787-182-8. The appropriate fractions were combined and evaporated under vacuum and the components were characterised by their chromatographic and spectroscopic properties as summarised in Tables 1–6.

EXAMPLE 7

Isolation of N787-182-12

Fraction 2 as obtained by the method described in Example 1 was found to contain N787-182-12 by HPLC. This material (49 mg) was chromatographed on an Ultrasphere ODS (5 m) (Trademark - Beckman) HPLC column (10×250 mm) eluting with water:methanol 15:85 at 3 mls per minute. The fractions eluting between 43 and 50 minutes were combined and evaporated under vacuum. The crude N787-182-12 was re-purified by chromatography using the same conditions described above to give pure N787-182-12 which was characterised by its chromatographic and spectroscopic properties as summarised in Tables 1–6.

EXAMPLE 8

Isolation of N787-182-6

Fractions obtained by the procedure described in Example 3 which were found by HPLC to be rich in factor N787-182-6 were combined. Non-polar impurities were removed by further chromatography on silica gel (Kieselgel 60,230–400 mesh, Merck) eluting initially with dichloromethane-hexane 1:1. Material enriched with N787-182-6 was then recovered by elution with ethyl acetate. After removal of the solvent under vacuum this material (150 mg) was chromatographed on a C18 Zorbax ODS (8 μm) (Trademark, Dupont) HPLC column (21.2×250 mm) eluting with methanol:water 80:20 at 9 mls per minute. The fractions eluting between 22 and 25 minutes were combined and evaporated under vacuum to give pure N787-182-6 which was characterised by its Tables 1–6.

EXAMPLE 9

Isolation of N787-182-9

Fractions obtained by the procedure described in Example 3 which were found by HPLC to be rich in factor N787-182-9 were combined. Non-polar impurities were removed by further chromatography on silica gel (Kieselgel 60, 230–400 mesh, Merck) eluting initially with dichloromethane-hexane 1:1. Material enriched with N787-182-9 was then recovered by elution with ethyl acetate. After removal of the solvent under vacuum this material (150 mg) was chromatographed on a C18 Zorbax ODS (8 m) (Trademark, Dupont) HPLC column (21.2×250 mm) eluting with methanol:water 80:20 at 9 mls per minute for 80 minutes followed by methanol:water 85:15 at 9 mls per minute for 60 minutes. Fractions eluting between 90 and 100 minutes were combined and evaporated under vacuum to give pure N787-182-9 which was characterised by its chromatographic and spectroscopic properties as summarised in Tables 1–6.

EXAMPLE 10

Preparation of N787-182-12 from N787-182-5

To a solution of N787-182-5 (93 rag) in anhydrous dichloromethane (1 ml) under an atmosphere of nitrogen at 20° C. was added anhydrous pyridine (500 μl) and p-tolyl-chlorothionoformate (200 μl). The yellow solution was magnetically stirred at room temperature for 2 hours after which time no starting material remained by thin layer chromatography. Any precipitate forming during the course of the reaction was re-dissolved by small additions of dichloromethane. The reaction mixture was poured into ice cold 0.1 M hydrochloric acid and extracted three times with dichloromethane. The organic layer was dried over anhydrous sodium sulphate and evaporated under vacuum. The crude thionocarbonate product was purified by column chromatography on silica gel (10 g Kieselgel 60, 230–400 mesh, Merck) eluting initially with dichloromethane and subsequently with a mixture of dichloromethane and ethyl acetate (4:1). The desired fractions were combined, evaporated under vacuum and the residue dissolved in anhydrous toluene (2 5 ml) Tri-n-butyltin hydride (500 µl) and azobisisobutyronitrile (1 mg) were added and the mixture was heated under reflux under nitrogen for 2 hours, when thin layer chromatography indicated complete reaction. The solvent was evaporated under vacuum and the desired product purified by column chromatography on silica gel (15 g Kieselgel 60, 230–400 mesh, Merck) eluting with dichloromethane. Final purification was achieved by chromatography on a C18 Zorbax ODS (8 µm) (Trademark, Dupont) HPLC column (2×250 mm) eluting with methanol:water (85:15) at 9 mls per minute. Fractions eluting between 56 and 68 minutes were combined and evaporated under vacuum to give pure N787-182-12 (25 mg) identical to that obtained in Example 7.

EXAMPLE 11

Preparation of Compound 15 from N787-182-12

To a solution of N787-82-12 (9 mg) in methanol (8 ml) was added water (2 ml) and p-toluenesulphonic acid (5 mg). The solution was heated under reflux for 12 days and the solvent was evaporated under vacuum. The residue was partially purified by passage through a plug of silica gel (0.6 g) eluting with dichloromethane-ethyl acetate (1:1) and finally purified by chromatography on an Ultrasphere ODS (5 µm) (Trademark - Beckman) HPLC column (10×250 mm) eluting with water-methanol (15:85) at 3 mls per minute. Fractions eluting between 33 and 45 minutes were combined and evaporated under vacuum to give pure Compound 15 (1.74 mg) characterised by its spectroscopic properties as summarised in Tables 2–6.

EXAMPLE 12

Preparation of Compound 14 From N787-182-9

A solution of N787-182-9 (10 mg) in anhydrous ether (2 ml) under nitrogen was cooled to −23° C. and a solution of lithium aluminium hydride in ether (1M, Aldrich Chemical Company, 200 µl) was added dropwise. After 20 minutes, ethyl acetate (100 µl) was added and, after warming to room temperature, he mixture was poured into ice cold hydrochloric acid (0.1 M) and extracted with diethyl ether. The yellow organic solution was dried over anhydrous sodium sulphate and evaporated under vacuum. The crude product was chromatographed on silica gel (Kieselgel 60, Merck, 230–400 mesh) eluting with dichloromethane-ethyl acetate (1:1) to give pure Compound 14 (8.0 mg) characterised by its spectroscopic properties as summarised in Tables 2–6.

EXAMPLE 13

Preparation of Compound 13 from N787–182-4

To a solution of N787-182-4 (13.4 mg) in a mixture of methanol and dioxane (2:1) (2 ml) was added 3N hydrochloric acid (150 µl). The mixture was heated under reflux for 5 days and the solvent was evaporated under vacuum. The crude product was purified by chromatography n an Ultrasphere-ODS (5 µm) (Trademark-Beckman) HPLC column (10×250 mm) eluting with water:methanol (30:70) at 3 mls per minute. Fractions eluting between 10 and 19 minutes were combined and evaporated under vacuum to give pure Compound 13 (4.3 mg), characterised by its spectroscopic properties as summarised in Tables 2–6.

EXAMPLE 14

Anthelmintic Activity

Anthelmintic activity was evaluated against *Caenorhabditis elegans* using the in vitro screening test described by K. G. Simpkin and G. L. Coles in Parasitology, 1979, 79, 19. Antibiotic N787-182 factors 4, 6, 8 and 9 killed at least 95% of the worms at a well concentration of 0.01 parts per million.

EXAMPLE 15

Insecticidal Activity

Activity against the larval stage of the blowfly *Lucilia cuprina* (O strain) is demonstrated using a standard procedure in which first instar larvae are kept in contact with filter paper treated with test compound. The test compound is first applied to the paper as an acetone solution. The treated filter papers are then placed into tubes containing 1 ml of newborn calf serum and the first instars are added. Antibiotic N787-182 factors 4, 6, 8 and 9 killed 100% of the larvae when applied to the filter paper at a level of 1 mg per square meter.

TABLE 1

Thin layer chromatography –$R_F$ values for selected N787-182 factors
Thin layer chromatography was performed using Merck 5735 Kieselgel 60 silica plates and developed using dichloromethane:ethyl acetate 4:1 and visualised by quenching of UV fluorescence at 254 nm.

| Factor | $R_F$ |
| --- | --- |
| 1 | 0.07 |
| 3 | 0.10 |
| 4 | 0.10 |
| 5 | 0.30 |
| 6 | 0.23 |
| 7 | 0.38 |
| 8 | 0.17 |
| 9 | 0.48 |
| 11 | 0.40 |
| 12 | 0.60 |

TABLE 2

Ultraviolet Spectral Properties of N787-182 factors 1–12 and Compounds 13–15

| N787-182 Factor | UV absorbance maxima (nm) (water methanol solution |
| --- | --- |
| 1 | 240 (sh), 246, 255 (sh) |
| 2 | 240 (sh), 246, 255 (sh) |
| 3 | 240 (sh), 246, 255 (sh) |
| 4 | 239 (sh), 246, 255 (sh) |
| 5 | 239 (sh), 246, 255 (sh) |
| 6 | 238 (sh), 244, 253 (sh) |
| 7 | 239 (sh), 246, 255 (sh) |
| 8 | 238 (sh), 244, 253 (sh) |
| 9 | 238 (sh), 244, 253 (sh) |
| 10 | 239 (sh), 245, 255 (sh) |
| 11 | 239 (sh), 246, 255 (sh) |
| 12 | 240 (sh), 246, 254 (sh) |
| Compound 13 | 238 (sh), 245, 254 (sh) |
| Compound 14 | 238 (sh), 244, 253 (sh) |
| Compound 15 | 238 (sh), 245, 254 (sh) |

TABLE 3

Electron Impact Spectrometry: Principal Fragment Ions for N-787-182 Factors 1-12 and Compounds 13–15

N787-182-1 m/e 614 ($M^+$), 596 $(M—H_2O)^+$

N787-182-3 m/e 682 (M—H$_2$O)$^+$

N787-182-5 m/e 684 (M$^+$), 666 (M—H$_2$O)$^+$, 597, 578, 456, 436,

N787-182-7 m/e 770 (M$^+$), 752 (M—H$_2$O)$^+$, 682, 151

N787-182-8 m/e 670 (M$^+$), 652 (M—H$_2$O)$^+$, 634 (M—2H$_2$O)$^+$, 560, 454, 436, 151

N787-182-9 m/e 654 (M$^+$), 566, 548, 530, 151

N787-182-10 m/e 766 (M–H$_2$O)$^+$, 682

N787-182-11 m/e 684 (M$^+$), 666 (M–H$_2$O)$^+$, 634, 542, 524, 454, 436, 151

N787-182-12 m/e 668 (M$^+$), 580

Compound 13 m/e 600 (M$^+$), 582 (M—H$_2$O)$^+$, 564 (M—2H$_2$O)$^+$

Compound 14 m/e 584 (M$^+$), 568 (M—HO)$^+$, 548 (M—2H$_2$O)$^+$

Compound 15 m/e 598 (M$^+$), 580 (M—H$_2$O)$^+$

TABLE 4

Fast Atom Bombardment Mass Spectroscopy

N787-182-1: m/e 637 (M + Na$^+$) (Theoretical 637)

N787-182-2: m/e 709 (M + Na$^+$) (Theoretical 709)

N787-182-3: m/e 723 (M + Na$^+$) (Theoretical 723)

N787-182-5: m/e 707 (M + Na$^+$) (Theoretical 707)

N787-182-6: m/e 779 (M + Na$^+$) (Theoretical 779)

N787-182-8: m/e 693 (M + Na$^+$) (Theoretical 693)

M787-182-9: m/e 677 (M + Na$^+$) (Theoretical 677)

N787-182-11: m/e 707 (M + Na$^+$) (Theoretical 707)

Compound 13: m/e 623 (M + Na$^+$) (Theoretical 623)

Compound 14: m/e 607 (M + Na$^+$) (Theoretical 607)

Compound 15: m/e 621 (M +Na$^+$) (Theoretical 621)

TABLE 5

Chemical Ionisation (CI$^-$) Mass Spectroscopy: Principal Ions

N787-182-4: m/e 671 (M + H)$^-$, 582

N787-182-7: m/e 769 (M − H)$^-$, 682, 652, 87

N787-182-10: m/e 78 (M)$^-$, 754, 682, 652, 101, 87

N787-182-11: m/e 685 (M + H)$^-$, 653, 635

N787-182-12: m/e 581 (M + H)$^-$ 87

TABLE 6

Nuclear Magnetic Resonance Spectroscopy (CDCl$_3$):

N787-182-1: 5.9–5.7 (m, 2H), 5.5–5.25 (m, 5H), 4.75–4.6 (m, 2H), 4.05 (d, 1H), 3.97 (m, 1H), 3.75 (d, J=11, 1H), 3.53 (s, 3H), 3.42 (d, 1H), 1.85 (bs, 3H), 1.68 (d, 3H), 1.15 (d, 3H), 0.72 (d, 3H).

N787-182-2: 5.9–5.7 (m, 2H), 5.55–5.2 (m, 5H), 4.95 (t, 1H), 4.68 (m, 2H), 4.29 (t, 1H), 3.98 (d, 1H), 3.83 (s, 1H), 3.73 (d, 1H), 3.60 (d, 1H), 2.62 (heptet, 1H), 1.90 (bs, 3H), 1.65 (d, 3H), 1.22 (d, 6H), 1.17 (d, 3H), 0.95 (q, 1H), 0.70 (d, 3H).

N787-182-3: 5.9–5.7 (m, 2H), 5.48 (q, 1H), 5.42 (bs, 1H), 5.4–5.2 (m, 3H), 4.95 (t, 1H), 4.68 (m, 2H), 4.05 (d, 1H), 4.00 (m, 1H), 3.90 (s, 1H), 3.75 (d, J=11, 1H), 3.60 (d, 1H), 3.53 (s, 3H), 3.45 (m, 1H), 3.25 (m, 1H), 2.63 (heptet, 1H), 2.40 (m, 1H), 1.85 (bs, 3H), 1.70 (d, 3H), 1.17 (d, 3H), 0.98 .(q, 1H), 0.70 (d, 3H).

N787-182-4: 5.9–5.7 m, 2H), 5.45–5.3 (m, 5H), 4.95 (d, 1H), 4.7 (m, 2H), 4.32 (m, 1H), 3.98 (d, 1H), 3.63 (m, 1H), 3.39 (d, 1H), 3.30 (m, 1H), 2.67–2.5 (m, 2H), 2.4–2.2 (m, 2H), 1.90 (s, 3H), 1.67 (d, 3H), 1.60 (s, H), 1.58 (s, 3H), 1.42 (q, 1H), 1.20 (d, 3H), 1.18 (d, 3H), 1.02 (d, 3H), 0.92 (q, 1H), 0.70 (d, 3H).

N787-182-5: 5.9–5.7 (m, 2H); 5.45–5.3 (m, 5H), 4.95 (d, 1H), 4.7 (m, 2H), 4.05 (d, 1H), 3.97 (m, 1H), 3.62 (m, 1H), 3.53 (s, 3H), 3.38 (d, 1H), 3.33 (m, 1H), 2.6 (m, 1H), 2.57 (heptet, 1H), 2.4–2.2 (m, 2H), 1.82 (bs, 3H), 1.65 (d, 3H), 1.58 (s, 3H), 1.56 (s, 3H), 1.42 (q, 1H), 1.2 (d, 3H), 1.18 (d, 3H), 1.02 (d, 3H), 0.93 (q, 1H), 0.70 (3H, d).

N787-182-6: 5.82 (dd, J=11.3, 14.4, 1H), 5.75 (bd, J=11.3, 1H), 5.43 (q, J=6.6, 1H), 5.42 (bs, 1H), 5.36 (dd, J=12, 4, 1H), 5.31 (dd, J=14.4, 10.2, 1H), 5.29 (m, 1H), 4.92 (d, J=10.5, 1H), 4.91 (t, J=10, 1H), 4.68 (m, 2H), 4.28 (t, J=7.2, 1H), 3.95 (d, J=6.3, 1H), 3.84 (s, 1H), 3.59 (m, 1H), 3.54 (d, J=10.4, 1H), 3.27 (bs, 1H), 3.20 (dd, J=11.5, 9.5, 1H), 2.60 (heptet, J=7, 1H), 2.58 (m, 1H), 2.55 (heptet, J=7, 1H), 2.31 (d, J=8.3), 2.28–2.20 (m, 2H), 1.87 (bs, 3H), 1.66 (d, J=6.6 3H), 1.59 (s, 3H), 1.54 (s, 3H), 1.20 (d, J=6.6, 3H), 1.19 (d, J=6.6, 3H), 1.18 (d, J=6.6, 3H), 1.17 (d, J=6.6, 3H), 0.99 (d, J=6.6, 3H), 0.91 (q, J=12, 1H), 0.68 (d, J=6.6, 3H).

N787-182-7: 5.9–5.7 (m, 2H), 5.5–5.25 (m, 5H), 4.95 (dd, 1H), 4.95 (d, 1H), 4.78–4.62 (m, 2H), 4.05 (d, 1H), 3.99 (m, 1H), 3.58 (d, 1H), 3.52 (s, 3H), 3.35 (m, 1H), 3.23 (m, 1H), 2.7–2.5 (m, 3H), 1.83 (bs, 3H), 1.02 (d, 3H), 0.70 (d, 3H).

N787-182-8: 5.8–5.7 (m, 2H), 5.45 (dq, J=6.7, 1.2, 1H), 5.42 (bs, 1H), 5.36–5.27 (m, 2H), 4.97 (m, 1H), 4.93 (dd, J=10.6, 9.5, 1H), 4.72–4.65 (m, 2H), 4.29 (bt, J=6, 1H), 3.95 (d, J=6.2, 1H), 3.89 (s 1H), 3.61 (m, 1H), 3.58 (d, J=10.4 1H) 3.27 (sextet, J=2.3, 1H), 3.21 (dd, J=11.2, 9.6, 1H), 2.61 (heptet, J=7, 1H), 2.43 (m, 1H), 2.33 (d, J=7.9, 1H), 2.27–2.18 (m, 3H), 1.88 (bs, 3H), 1.66 (dd, J=6.7, 1, 3H), 1.60 (s, 3H), 1.54 (s, 3H), 1.20 (d, J=7, 3H), 1.20 (d, J=6.95, 3H), 1.00 (d, J=6.7, 3H), 0. 90 (q, J=12.4, 1H), 0.68 (d, J=6.6, 3H).

N787-182-9: 5.9–5.75 (m, 2H), 5.45–5.3 (m, 5H), 4.94 (d, J=11, 1H), 4.70 (m, 2H), 4.32 (bd, J=6, 1H), 3.98 (d, J=6.5, 1H), 3.57 (m, 1H), 3.44 (d, J=8, 1H), 3.29 (m, 1H), 2.65–2.5 (m, 2H), 1.89 (bs, 3H), 1.67 (d, J=7, 3H), 1.61 (s, 3H), 1.56 (s, 3H), 1.20 (d, J=7.5, 3H), 1.18 (d, J=6.5, 3H), 1.02 (d, J=7, 3H), 0.70 (bs, 3H).

N787-182-10: 5.9–5.7 (m, 2), 5.5–5.25 (m, 5H), 4.93 (m, 2H), 4.68 (m, 2H), 4.05 (d, 1H), 3.98 (m, 1H), 3.57 (d, 1H), 3.52 (s, 3H), 3.23 (m, 1H), 2.7–2.5 (m, 3H), 1.86 (bs, 3H), 0.71 (d, 3H).

N787-182-11: 5.82–5.7 (m, 2H), 5.48 (q, 1H), 5.43 (bs, 1H), 5.4–5.25 (m, 2H), 4.98 (m, 1H), 4.95 (dd, 1H), 4.78–4.6 (m, 2H), 4.05 (d, 1H), 3.98 (m, 1H), 4.95 (s, 1H), 3.60 (d, 1H), 3.52 (s, 3H), 3.35 (m, 1H), 3.25 (d, 1H), 2.63 (heptet, 1H), 2.45 (m, 1H), 1.85 (bs, 3H), 1.68 (d, 3H), 1.60 (s, 3H), 1.55 (s, 3H), 1.20 (d, 3H), 1.00 (d, 3H), 0.70 (d, 3H).

N787-182-12: 5.9–5.7 (m, 2H), 5.5–5.3 (m, 5H), 4.95 (d, 1H), 4.7 (m H), 4 06 (d, 1H) 3 98 (m, 1H), 3 51 (s, 3H), 3 33 (m, 1H), 2.58 (heptet, 1H), 1.82 (bs, 3H), 1.65 (d, 3H), 1.20 (d, 3H), 1.18 (d, 3H), 1.02 (d, 3H), 0.69 (bs, 3H).

Compound 13: 5.82–5.72 (m, 2H), 5.45–5.23 (m, 5H), 4.73–4.64 (m, 2H), 4.29 (t, J=6.3, 1H), 3.95 (d, J=6, 1H), 3.88 (s, 1H), 3.71 (d, J=9.7, 1H), 3.66–3.59 (m, 1H), 3.39 (d, J=10 2, 1H), 3.35 (dr, J=4.4, 10.8, 1H), 3.26 (sextet J=2.2, 1H) 1.87 (bs, 3H), 1.65 (d, J=6.5, 3H), 1.41 (q, J=12, 1H), 1.25 (bs, 3H), 1.12 (d, J=6.5, 3H), 0.91 (q, J=12, 1H), 0.70 (d, J=6.6, 3H).

Compound 14: 5.85–5.72 (m, 2H), 5.48–5.25 (m, 5H), 4.78–4.65 (m, 2H), 4.31 (t, 1H), 3.99 (d, 1H), 3.97 (s, 1H), 3.74 (d, 1H), 3.60 (m, 1H), 3.48 (d, 1H), 3.30 (sextet, 1H), 2.45–2.28 (m, 4H), 2.06 (m, 1H), 1.90 (bs, 3H), 1.68 (d, 3H), 1.36 (t, 1H), 1.15 (d, 3H), 0.92 (q, 1H), 0.72 (m, 3H).

Compound 15: 5.79 (dd, J=14.5, 11.3, 1H), 5.71 (dr, J=11.3, 2.3, 1H), 5.43–5.23 (m, 5H), 4.69 (dd, J=14.5, 2.4, 1H), 4.63 (dd, J=14.5, 2.4, 1H), 4.01 (d, J=5.6, 1H), 3.97 (bs, 1H), 3.70 (d, J=10, 1H), 3.55–3.52 (m, 1H), 3.50 (s, 3H), 3.46–3.43 (m, 1H), 3.30 (m, 1H), 2.40–2.27 (m, 3H), 2.1–2.0 (m, 1H), 1.81 (bs, 3H), 1.64 (d, J=6.7, 3H), 1.34 (t, J=11.8, 1H), 1.12 (d, J=6.5, 3H), 0.90 (q, J=12.5, 1H), 0.68 (m, 3H).

What is claimed is:

1. A biologically pure culture of *Streptomyces hygroscopicus* having all of the identifying characteristics of ATCC 53718 or a mutant thereof capable of producing a compound of the formula

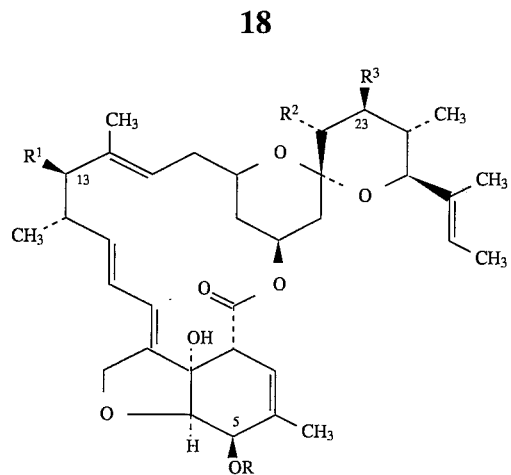

wherein R is H;
$R^1$ is H or OCOCH(CH$_3$)$_2$;
$R^2$ is OH; and
$R^3$ is H or OCOCH(CH$_3$)$_2$; and $R^1$ and $R^3$ may not both be H,
upon cultivation in an aqueous nutrient medium containing assimilable sources of carbon, nitrogen and inorganic salts.

2. A biologically pure culture of *Streptomyces hygroscopicus* ATCC 53718.

* * * * *